US010585058B2

(12) United States Patent
Cobianu et al.

(10) Patent No.: US 10,585,058 B2
(45) Date of Patent: Mar. 10, 2020

(54) FET BASED HUMIDITY SENSOR WITH BARRIER LAYER PROTECTING GATE DIELECTRIC

(71) Applicant: Honeywell International Inc., Morris Plains, NJ (US)

(72) Inventors: Cornel Cobianu, Bucharest (RO); Alisa Stratulat, Bucharest (RO); Bogdan Serban, Bucharest (RO); Octavian Buiu, Bucharest (RO); Cazimir Gabriel Bostan, Bucharest (RO); Mihai Brezeanu, Bucharest (RO); Stefan Dan Costea, Bucharest (RO); Richard Davis, Plano, TX (US)

(73) Assignee: Honeywell International Inc., Morris Plains, NJ (US)

( * ) Notice: Subject to any disclaimer, the term of this patent is extended or adjusted under 35 U.S.C. 154(b) by 344 days.

(21) Appl. No.: 15/594,184

(22) Filed: May 12, 2017

(65) Prior Publication Data

US 2017/0328855 A1    Nov. 16, 2017

(30) Foreign Application Priority Data

May 13, 2016  (EP) .................................. 16169738

(51) Int. Cl.
*G01N 27/22* (2006.01)
*G01N 27/414* (2006.01)
(Continued)

(52) U.S. Cl.
CPC ....... *G01N 27/223* (2013.01); *G01N 27/4141* (2013.01); *H01L 29/4966* (2013.01); *H01L 29/51* (2013.01)

(58) Field of Classification Search
CPC .................. G01N 27/223; G01N 27/4141
(Continued)

(56) References Cited

U.S. PATENT DOCUMENTS

| 4,057,823 A | 11/1977 | Burkhardt et al. |
| 4,366,709 A | 1/1983 | Eiermann et al. |

(Continued)

FOREIGN PATENT DOCUMENTS

| CN | 1455250 A | 11/2003 |
| CN | 1651910 A | 8/2005 |

(Continued)

OTHER PUBLICATIONS

Noboru Yamazoe, Yasuhiro Shimtzu, Humidity Sensors principles and Applications; Sensors and Actuators, 10 (1986) pp. 379-398.
(Continued)

*Primary Examiner* — John Fitzgerald
*Assistant Examiner* — Rodney T Frank
(74) *Attorney, Agent, or Firm* — Craige Thompson; Thompson Patent Law; Vincent Musgrove

(57) ABSTRACT

An illustrative humidity sensor may include a substrate having a source and a drain, wherein the drain is laterally spaced from the source. A gate stack is provided in the space between the source and the drain to form a transistor. The gate stack may include a gate insulator situated on the substrate to form a gate insulator/substrate interface. The gate stack may further include a barrier layer above the gate insulator. The barrier layer may be configured to act as a barrier to mobile charge, humidity and/or other contaminates, and may help prevent such contaminates from reaching the gate insulator/substrate interface. The gate stack may further include a humidity sensing layer above the barrier layer. The humidity sensing layer, when exposed to humidity, may modulate the conduction channel in the substrate under the gate insulator and between the source and the drain. In some cases, the humidity level may be determined by monitoring the current flowing between the source and drain.

20 Claims, 2 Drawing Sheets

(51) Int. Cl.
*H01L 29/49* (2006.01)
*H01L 29/51* (2006.01)

(58) Field of Classification Search
USPC ........................................ 73/335.04
See application file for complete search history.

(56) References Cited

U.S. PATENT DOCUMENTS

| | | |
|---|---|---|
| 4,429,343 A | 1/1984 | Freud |
| 4,470,096 A | 9/1984 | Guertin |
| 4,564,228 A | 1/1986 | Kohlen |
| 4,564,882 A | 1/1986 | Baxter et al. |
| 4,638,346 A | 1/1987 | Inami et al. |
| 4,938,995 A | 7/1990 | Giordano et al. |
| 5,161,085 A | 11/1992 | Sakai et al. |
| 5,408,381 A | 4/1995 | Thoma et al. |
| 5,529,279 A | 6/1996 | Beatty et al. |
| 5,535,633 A | 7/1996 | Kofoed et al. |
| 5,702,773 A | 12/1997 | Endo |
| 5,780,121 A | 7/1998 | Endo |
| 5,795,655 A | 8/1998 | Endo |
| 6,150,681 A | 11/2000 | Allen |
| 6,222,376 B1 | 4/2001 | Tenney, III |
| 6,245,489 B1 | 6/2001 | Baklanov et al. |
| 6,470,741 B1 | 10/2002 | Fathollahzadeh |
| 6,614,241 B2 | 9/2003 | Schmitt et al. |
| 6,615,667 B2 | 9/2003 | Smith |
| 6,647,782 B2 | 11/2003 | Toyoda |
| 6,658,946 B2 | 12/2003 | Lipscomb et al. |
| 6,690,569 B1 | 2/2004 | Mayer et al. |
| 6,724,612 B2 | 4/2004 | Davis et al. |
| 6,867,602 B2 | 3/2005 | Davis et al. |
| 6,945,123 B1 | 9/2005 | Kuehl et al. |
| 7,042,091 B2 | 5/2006 | Baklanov et al. |
| 7,111,518 B1 | 9/2006 | Allen et al. |
| 7,115,531 B2 | 10/2006 | Shaffer, II et al. |
| 7,176,700 B2 | 2/2007 | Itakura et al. |
| 7,233,000 B2 | 6/2007 | Nassiopoulou et al. |
| 7,278,309 B2 | 10/2007 | Dmytriw et al. |
| 7,280,927 B1 | 10/2007 | Dmytriw |
| 7,493,822 B2 | 2/2009 | Stewart et al. |
| 7,563,692 B2 | 7/2009 | Fortin et al. |
| 7,635,091 B2 | 12/2009 | Engler et al. |
| 7,678,600 B2 | 3/2010 | Villa et al. |
| 7,683,636 B2 | 3/2010 | Alimi et al. |
| 7,703,339 B2 | 4/2010 | Sulouff, Jr. et al. |
| 7,710,128 B2 | 5/2010 | Alimi et al. |
| 7,713,772 B2 | 5/2010 | Vanha et al. |
| 7,769,557 B2 | 8/2010 | Bey et al. |
| 7,924,028 B2 | 4/2011 | Alimi et al. |
| 8,047,074 B2 | 11/2011 | Jun et al. |
| 8,104,355 B2 | 1/2012 | Minamitani et al. |
| 8,601,879 B2 | 12/2013 | Okada |
| 8,616,065 B2 | 12/2013 | Stewart et al. |
| 8,975,671 B2 | 3/2015 | Ten Have |
| 9,080,907 B2 | 7/2015 | Haneef et al. |
| 9,156,676 B2 | 10/2015 | Stewart et al. |
| 9,513,242 B2 | 12/2016 | Beck et al. |
| 2003/0010119 A1 | 1/2003 | Toyoda |
| 2004/0008471 A1 | 1/2004 | Davis et al. |
| 2004/0177685 A1 | 9/2004 | Yokura et al. |
| 2007/0251292 A1 | 11/2007 | Beck et al. |
| 2008/0134753 A1 | 6/2008 | Jun et al. |
| 2009/0108852 A1 | 4/2009 | Alimi et al. |
| 2010/0140669 A1 | 6/2010 | Xie |
| 2011/0107832 A1 | 5/2011 | Sakuma |
| 2011/0252882 A1 | 10/2011 | Beck et al. |
| 2012/0205653 A1 | 8/2012 | Nishikage et al. |
| 2013/0001710 A1 | 1/2013 | Daneman et al. |
| 2013/0139584 A1 | 6/2013 | Qasimi et al. |
| 2013/0139587 A1 | 6/2013 | Le Neel et al. |
| 2014/0073927 A1 | 3/2014 | Chung |
| 2014/0210036 A1 | 7/2014 | Sunier et al. |
| 2014/0298913 A1 | 10/2014 | Stewart et al. |
| 2015/0021716 A1 | 1/2015 | Lee et al. |
| 2016/0077028 A1 | 3/2016 | Beck et al. |
| 2016/0202201 A1* | 7/2016 | Cobianu ............ G01N 27/223 73/335.04 |

FOREIGN PATENT DOCUMENTS

| | | |
|---|---|---|
| CN | 102213606 A | 10/2011 |
| CN | 101932928 B | 2/2013 |
| CN | 205944090 U | 2/2017 |
| CN | 107449811 A | 12/2017 |
| CN | 107533027 A | 1/2018 |
| EP | 0981737 A1 | 3/2000 |
| EP | 1695073 B1 | 5/2012 |
| EP | 2203738 B1 | 9/2017 |
| EP | 3244201 A1 | 11/2017 |
| EP | 3259581 A1 | 12/2017 |
| FR | 2991456 A1 | 12/2013 |
| JP | 60181645 A | 9/1985 |
| JP | S60181645 A | 9/1985 |
| JP | 2003004683 A | 1/2003 |
| JP | 2009050376 A | 3/2009 |
| KR | 1020050076524 A | 7/2005 |
| WO | 2008030913 A2 | 3/2008 |
| WO | 2009055355 A3 | 4/2009 |
| WO | 2009055355 A3 | 6/2009 |
| WO | 2010033358 A2 | 3/2010 |
| WO | 2016040482 A1 | 3/2016 |
| WO | 2016134079 A1 | 8/2016 |

OTHER PUBLICATIONS

New Microhumidity Field-effect transistor sensor in ppm v. level; Review of Scientific Instruments; vol. 70, No. 2; Feb. 1999, pp. 565-1567.

European search report; Honeywell International Inc., dated Oct. 26, 2016, Application No. 1616738.8, 7 pages.

Sung Pil Lee, Ji Gong Lee and Shaestagir Chowdhury, CMOS Humidity Sensor System Using Carbon Nitride Film as Sensing Materials; vol. 8, No. 4 Apr. 14, 2008 pp. 2662-2672.

International Application No. PCT/US2016/018355, International Search Report, dated May 12, 2016, 4 pages.

International Application No. PCT/US2016/018355, Written Opinion of the International Searching Authority, dated May 12, 2016, 8 pages.

Kuroiwa et al., "A Thin Film Polyimide Based Capacitive Type Relative Humidity Sensor", Sensors and Actuators B: Chemical: International Journal Devoted to Research and Development of Physical and Chemical Transducers, Elsevier, S.A., CH, vol. B13, No. 1/03, May 1, 1993, pp. 89-91.

Wang et al., "On-Chip Integration of Acceleration, Pressure, and Temperature Composite Sensor with a Single-Sided Micromachining Technique," Journal of Microeletromechanical Systems, vol. 20, No. 1, pp. 42-52, Feb. 2011.

Zhang et al., "Fabrication of Thick Silicon Dioxide Layers Using DRIE, Oxidation and Trench Refill," IEEE, pp. 160-163, 2002.

International Application No. PCT/US2015/049185, International Search Report, dated Dec. 17, 2015, 4 pages.

International Application No. PCT/US2015/049185, Written Opinion of the International Searching Authority, dated Dec. 17, 2015, 8 pages.

Lee, "Fabrication and Sensing Properties of a Micro-Humidity Sensor System Using CMOS Technology," Electronic Materials Letters, vol. 6, No. 1, pp. 7-12, Mar. 31, 2010.

International Application No. PCT/US2015/049185, International Preliminary Report on Patentability, dated Mar. 14, 2017, 9 pages.

Europe Application No. 08842965.9, Decision to Grant a European patent, dated Aug. 31, 2017, 2 pages.

Europe Application No. 08842965.9, Supplementary European Search Report, dated Feb. 27, 2014, 3 pages.

Europe Application No. 08842965.9, Examination Report, dated Mar. 10, 2014, 7 pages.

Europe Application No. 08842965.9, Examination Report, dated Feb. 18, 2015, 3 pages.

(56) References Cited

OTHER PUBLICATIONS

Europe Application No. 08842965.9, Intention to Grant, dated May 12, 2017, 27 pages.
International Application No. PCT/US2016/018355, International Preliminary Report on Patentability, dated Aug. 22, 2017, 9 pages.
Europe Application No. 16708293.2, Communication pursuant to Rules 161(1) and 162 EPC, dated Oct. 17, 2017, 2 pages.
International Application No. PCT/US08/080586, Written Opinion of the International Searching Authority, dated May 12, 2009, 5 pages.
International Application No. PCT/US08/080586, International Preliminary Report on Patentability, dated Apr. 27, 2010, 6 pages.
China Patent Application No. 200880113107.X, First Office Action, dated Mar. 19, 2012, 8 pages.
China Patent Application No. 200880113107.X, Notification to Grant Patent Right, dated Oct. 16, 2012, 3 pages.
Noboru Yamazoe, Yasuhiro Shimtzu, Humidity Sensors principles and Applications; Sensors and Actuators, 1O (1986) pp. 379-398.
Europe Patent Application No. 16169738.8, European Search Report, dated Sep. 20, 2018, 5 pages.
Yamazoe N et al., Humidity sensors: Principles and applications, Sensors and Actuators, Elsevier, Switzerland, vol. 10, No. 3-4, Nov. 12, 1986, pp. 379-398, ISSN: 0250-6874, DOI: 10.1016/0250-6874(86)80055-5 [retrieved on Nov. 12, 1986].
Europe Patent Application No. 16169738.8, European Search Report dated Oct. 26, 2016, 11 pages.
U.S. Appl. No. 14/484,821, Restriction Requirement, dated Apr. 18, 2016, 6 pages.
U.S. Appl. No. 14/484,821, Notice of Allowance, dated Jul. 28, 2016, 10 pages.

\* cited by examiner

FET BASED HUMIDITY SENSOR WITH BARRIER LAYER PROTECTING GATE DIELECTRIC

The present application claims priority to Europe Patent Application Serial No. 16169738.8 filed May 13, 2016 and entitled "FET Based Humidity Sensor with Barrier Layer Protecting Gate Dielectric" which is incorporated herein by reference as if reproduced in its entirety.

TECHNICAL FIELD

The present disclosure relates to sensors, and more particularly to humidity sensors.

BACKGROUND

Capacitive and resistive type humidity sensors rely on the ability of a sensing material to quickly absorb and desorb water molecules. The absorbed moisture typically changes a physical property of the sensing material, and this change can be used to detect a change in humidity.

SUMMARY

The present disclosure relates to sensors, and more particularly to humidity sensors. An illustrative humidity sensor may be a FET based humidity sensor with a FET source and a drain formed in a substrate, with the drain laterally spaced from the source. A gate stack is provided in the space between the source and the drain to form a FET transistor. The gate stack may include a gate insulator situated on the substrate to form a gate insulator/substrate interface. The gate stack may further include a barrier layer above the gate insulator. The barrier layer may be configured to act as a barrier to mobile charge, humidity and/or other contaminates, and may help prevent such contaminates from reaching the gate insulator/substrate interface. The gate stack may further include a humidity sensing layer above the barrier layer. The humidity sensing layer, when exposed to humidity, may modulate the conduction channel in the substrate under the gate insulator between the source and the drain. In some cases, the humidity level may be determined by monitoring the current flowing between the source and drain. In some cases, the substrate may comprise silicon, the gate insulator may comprise $SiO_2$, the barrier layer may comprise one or more of $Ta_2O_5$, $Al_2O_3$, $HfO_2$ and silicon nitride ($Si_3N_4$), and the humidity sensing layer may comprise one or more of a polyimide and a polysulfone. It is contemplated that other suitable materials and/or material combinations may be used.

The preceding summary is provided to facilitate an understanding of some of the features of the present disclosure and is not intended to be a full description. A full appreciation of the disclosure can be gained by taking the entire specification, claims, drawings, and abstract as a whole.

BRIEF DESCRIPTION OF THE DRAWING

The disclosure may be more completely understood in consideration of the following description of various illustrative embodiments of the disclosure in connection with the accompanying drawings, in which.

Figure 1:
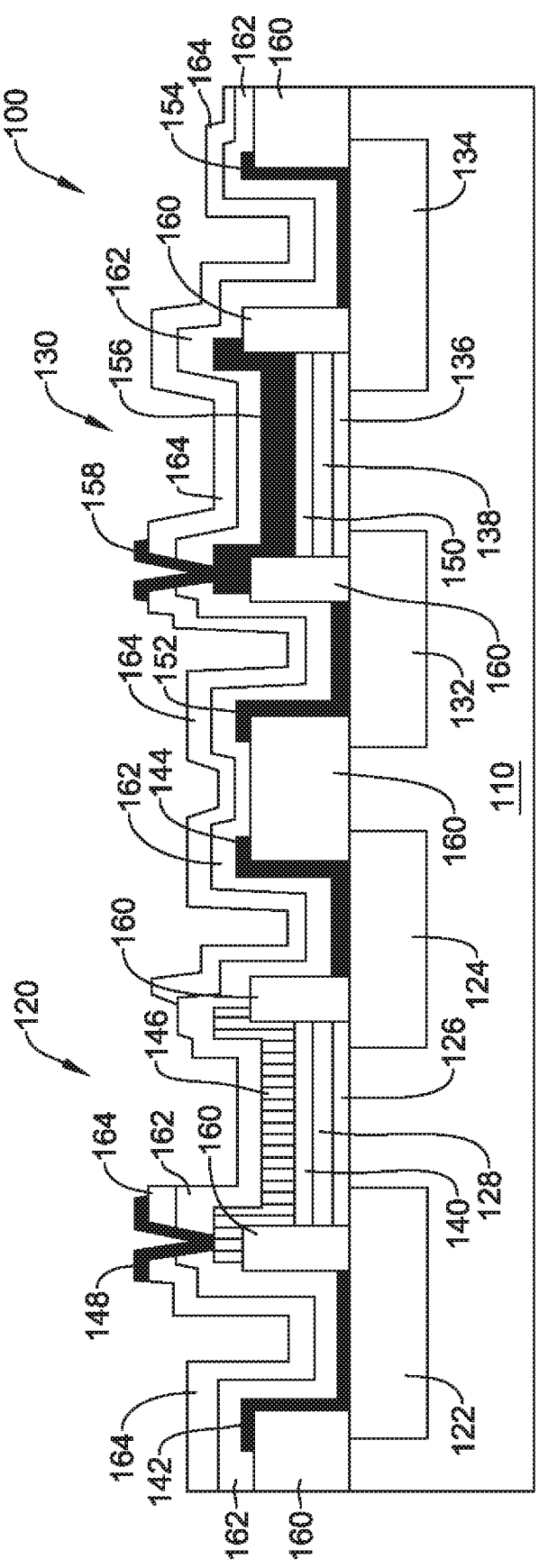
FIG. 1 is a schematic cross-sectional side view of an illustrative humidity sensor.

While the disclosure is amenable to various modifications and alternative forms, specifics thereof have been shown by way of example in the drawings and will be described in detail. It should be understood, however, that the intention is not to limit the disclosure to the particular illustrative embodiments described herein. On the contrary, the intention is to cover all modifications, equivalents, and alternatives falling within the spirit and scope of the disclosure.

DESCRIPTION

The present system and approach may incorporate one or more processors, computers, controllers, user interfaces, wireless and/or wire connections, and/or the like, in an implementation described and/or shown herein.

This description may provide one or more illustrative and specific examples or ways of implementing the present system and approach. There may be numerous other examples or ways of implementing the system and approach.

The following description should be read with reference to the drawings wherein like reference numerals indicate like elements throughout the several views. References to "over," "under," "top," and "bottom," etc., are relative terms and are made herein with respect to the drawings and do not necessarily correspond to any particular orientation in actual physical space. The description and drawings show several examples that are meant to be illustrative of the claimed disclosure.

Humidity sensors are used in a wide variety of applications. For example, humidity sensors are used for process control in industrial applications, air quality monitoring and control in homes and offices, and in automotive applications. Use of Relative Humidity (RH) sensors for cell phone and other mobile applications is expected to rise. Extensive use of humidity sensors in these and other applications may become more cost effective in part due to miniaturization and incorporation of such sensor technology into integrated circuits. Capacitive sensing principles can be implemented at the MOSFET transistor level to form a compact and inexpensive humidity sensor. In many cases, the humidity sensor and the associated electronics may be integrated on the same integrated circuit chip.

A FET transistor based humidity sensor may include a stacked gate that includes a sensing layer that modulates the conduction channel between the source and drain of the FET. The gate stack may include a gate insulator situated on a substrate to form a gate insulator/substrate interface. Given that the FET transistor based humidity sensor may be exposed to an ambient environment, and thus, to humidity and potentially more aggressive chemical (acid and base) contaminants and mobile charges (such as, but not limited, to sodium ions (Na+), potassium ions (K+), and/or magnesium ions (Mg2+)), which can reach and disrupt the insulator/substrate interface, it can be desirable to protect the insulator/substrate interface from direct contact with such contaminants, including humidity. As such, it is contemplated that the gate stack may include a barrier layer above the gate insulator. The barrier layer may be configured to act as a barrier to humidity, mobile charge and/or other contaminates, and may help prevent such contaminates from reaching and disrupting the gate insulator/substrate interface. Above the barrier layer may be a humidity sensing layer. The humidity sensing layer, when exposed to humidity, may modulate the conduction channel in the substrate between the source and the drain of the FET transistor based humidity sensor. In some cases, the humidity level may modulate the dielectric constant of the humidity sensing layer, which may modulate the threshold voltage of the FET transistor based humidity sensor. A gate electrode may be positioned over the humidity sensing layer. The gate electrode may be perforated or otherwise constructed to allow the humidity to reach the humidity sensing layer. Thus, by reaching the metal-sensing layer interface, the humidity can also change the work function difference between the perforated metal and the sensing layer, and thus the threshold voltage of the FET transistor, and thus the source-drain current of the FET transistor. The humidity level may then be determined by monitoring the current flowing between the source and drain of the FET transistor based humidity sensor.

FIG. 1 is a schematic cross-sectional side view of an illustrative humidity sensor 100 formed on a substrate. In this example shown, the substrate is a p-type silicon substrate 110. Illustrative sensor 100 includes a sensing field effect transistor (FET) 120 and a reference field effect transistor 130. In the example shown, FETs 120, 130 are n-channel FETs. However, sensor 100 may use p-channel FETs, sometimes in conjunction with an n-type substrate or formed in an n-well of a p-type silicon substrate 110, if desired.

In the example shown in FIG. 1, each of the sensing and reference n-channel FETs 120, 130 may have an n-type source 122, 132 and an n-type drain 124, 134. Extending between each source/drain pair may be a corresponding gate stack. In the example shown, the sensing and reference FETs 120, 130 incorporate a relatively thick (e.g. in the range of 1.5-2 micrometers (μm)) layer 160 of $SiO_2$, which in the example shown, defines the lateral edges of the gate stack and the source and drain regions of the sensing and reference FETs 120, 130. In some cases, the relatively thick layer 160 of $SiO_2$ may be grown by thermal oxidation of silicon substrate 110 before etching away portions to expose the source, drain and gate regions of the sensing and reference n-channel FETs 120, 130. In some instances, source contact electrodes 142, 152 and drain contact electrodes 144, 154 may be provided to make contact to the source and drain regions of the sensing and reference n-channel FETs 120, 130 as shown. The source contact electrodes 142, 152 and/or drain contact electrodes 144, 154 may be made from platinum, platinum/silicon, gold, aluminum, and/or any other suitable material.

The illustrative gate stacks include a lower gate insulating layer 126, 136 extending between the n-type source 122, 132 and n-type drain 124, 134, respectively, of the sensing and reference n-channel FETs 120, 130. In some cases, the lower gate insulating layer 126, 136 may be a thermally grown dielectric layer of $SiO_2$ in the gate regions exposed by the etched away portions of the relatively thick layer 160 of $SiO_2$. In some cases, the lower gate insulating layer 126, 136 may have a thickness that is less than 500 nanometers, less than 250 nanometers, less than 125 nanometers, less than 50 nanometers, or may have any other suitable thickness. In some cases, the lower gate insulating layer 126, 136 may have a thickness of about 100 nanometers.

The illustrative gate stack may further include a barrier layer 128, 138 disposed over the lower gate insulating layer 126, 136, respectively, of the sensing and reference n-channel FETs 120, 130. In some cases, the barrier layer 128, 138 may be a metal oxide layer (for example, but not limited to, tantalum pentoxide ($Ta_2O_5$), aluminum oxide ($Al_2O_3$), hafnium (IV) oxide ($HfO_2$)) and/or a silicon nitride ($Si_3N_4$) layer having a high chemical resistance and high gravimetric density with respect to the lower gate insulating layer (e.g. $SiO_2$). In some cases, the barrier layer 128, 138 may have a thickness in the range of 50-500 nanometers, 50-250 nanometers, 60-100 nanometers, or any other suitable thickness. The barrier layer 128, 138 may act as a mobile charge ($Na^+$, $K^+$, $Mg^{2+}$, $Ca^{2+}$, etc.) barrier, and/or may block penetration of other chemical contaminants (humidity included) from reaching the lower gate insulating layer 126, 136 and/or the lower gate insulating layer/substrate interface.

The illustrative gate stack may further include a humidity sensing layer 140, 150 above the barrier layer 128, 138 as shown. In some cases, the humidity sensing layer 140, 150 may be a hydrophobic dielectric polymer layer 140, 150 over the barrier layer 128, 138, respectively, of the sensing and reference FETs 120, 130. In some cases, the humidity sensing layer 140, 150 may be in the range of about 500-1000 nanometers thick, although other thicknesses may be used. In some cases, the hydrophobic dielectric polymer layer 140, 150 may be deposited by spin coating and then treated at 400 degrees C. in $N_2$.

The humidity sensing layer 150 of the reference FET 130 may be covered and sealed by a dense metal layer 156 forming a gate electrode for the reference FET 130. In some cases, the dense metal layer 156 may be a relatively thick gold or platinum layer of about 0.7-1.0 μm prepared by sputtering and lift-off technology. In contrast, the sensing FET 120 may include a porous metal layer forming a gate electrode 146. In some cases, the porous metal layer 146 may be an ultra-thin gold or platinum layer of about 50-100 nanometers thick prepared by sputtering and lift-off technology. The porous metal layer 146 of the sensing FET 120 may allow water vapor to be exchanged between the humidity sensing layer 140 of the sensing FET 120 and the ambient atmosphere. The porous metal layer 146 may have a thickness in the range of 25-300 nanometers, 30-200 nanometers, 40-80 nanometers, or 50-60 nanometers, although other thicknesses may be used. In some cases, the metal of gate electrodes 146, 156 may be formed from aluminum, platinum and/or gold. In some cases, a protective porous hydrophobic dielectric polymer layer 162 may be disposed over the surface of the sensor 100.

As can be seen, the humidity sensing layer 150 of the reference FET 130 is not exposed to the environment while the humidity sensing layer 140 of the sensing FET 120 is exposed to the environment. In some cases, the entire surface of the sensor 100, excluding the gate stack of the sensing FET 120, may be covered with a final passivation layer 164. The passivation layer 164 may include a barrier material such as, but not limited to, $SiO_2$, $Ta_2O_5$, $Al_2O_3$, $HfO_2$, or $Si_3N_4$ to help protect the sensor 100.

In the example shown, regions of the protective porous hydrophobic dielectric polymer layer 162 and the passivation layer 164 may be selectively removed to provide pathways to the gate electrodes 146, 156. Gate contacts 148, 158 may be provided through the pathways to make electrical contact with the gate electrodes 146, 156, respectively. The gate contacts 148, 158 may be formed from aluminum, copper, gold, titanium/gold (Ti/Au), or other materials, as desired.

In both the sensing and reference n-channel FETs 120, 130, the lower gate insulating layer 126, 136 and the lower gate insulating layer/substrate interface are sealed off from the environment by the substrate 110, the relatively thick layer 160 and barrier layer 128, 138. This helps protect the lower gate insulating layer 126, 136 and the lower gate insulating layer/substrate interface from degradation due to interactions with mobile charge ($Na^+$, $K^+$, $Mg^{2+}$, $Ca^{2+}$, etc.) and/or other chemical contaminants (humidit included) in the environment. In some cases, this can significantly increase the robustness of the humidity sensor 100.

The humidity sensing layer 140, 150 may be a hydrophobic dielectric polymer. Example hydrophobic dielectric polymers may be selected from among many polyimides and polysulfones, and in some cases may incorporate aromatic polyimides and polysulfones and/or cross-linked polyimides and polysulfones. When the polyimides or polysulfones are cross-linked polyimides or polysulfones, the cross-linking moiety usefully may be one of the group consisting of 2,2,3,3,4,4,5,5-octafluoro-1,6-hexanediol; 1,5-pentanediol; 1,10-decanediol; and 1,4-benzenedimethanol. Cross-linking may be accomplished by esterification with pendant carboxylic acid groups of the polyimides or polysulfones.

As non-limiting examples of suitable hydrophobic polymers, the following polymers may be prepared and used to construct the humidity sensing layer 140, 150;

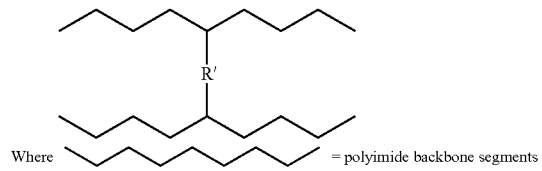

and an exemplary polyimide backbone segment may be

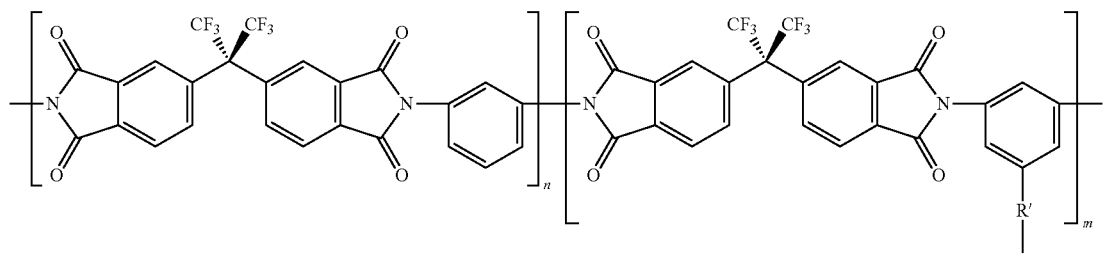

where R' is selected from:
—O$_2$CCH$_2$(CF$_2$)$_4$CH$_2$CO$_2$—; —O$_2$C(CH$_2$)$_5$CO$_2$—; —O$_2$C(CH$_2$)$_{10}$CO$_2$—; and —O$_2$CCH$_2$(C$_6$H$_4$)CH$_2$CO$_2$—.

As well as polysulfones such as:

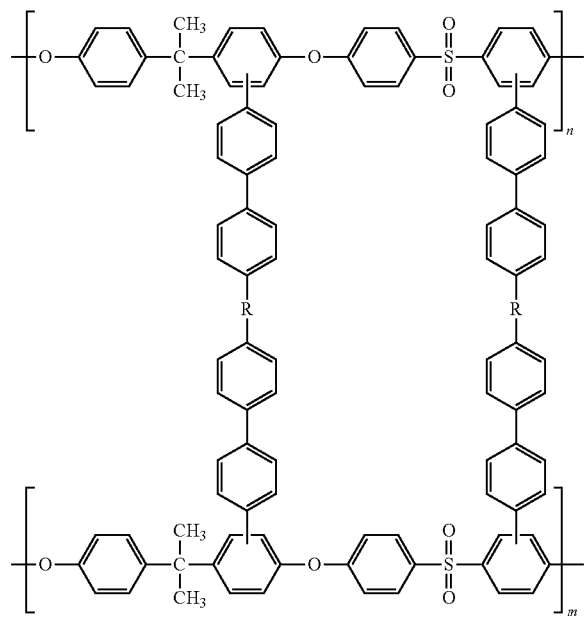

where R is selected from:
—O$_2$CCH$_2$(CF$_2$)$_4$CH$_2$CO$_2$—; —O$_2$C(CH$_2$)$_5$CO$_2$—; —O$_2$C(CH$_2$)$_{10}$CO$_2$—; and —O$_2$CCH$_2$(C$_6$H$_4$)CH$_2$CO$_2$—.

Exemplary humidity sensing layer 140, 150 may be applied to the barrier layer 128, 138 of the gate stack structures by spin coating and subsequently thermally treated at temperatures up to 400 degrees C. Patterning of the humidity sensing layer 140, 150 may be carried out by photoresist/etching processes although masked deposition may be used. The introduction of porosity into the deposited humidity sensing layer 140, 150 may allow the humidity sensing layer 140, 150 to be more responsive to changes in ambient humidity. It has been found that the thickness of the humidity sensing layer 140, 150 may affect the response time of the sensing FET 120 to changes in ambient humidity by delaying full equilibration. In some cases, the humidity sensing layer 140, 150 may be in the range of about 500-1000 nanometers thick, although other thicknesses are contemplated.

Figure 2:
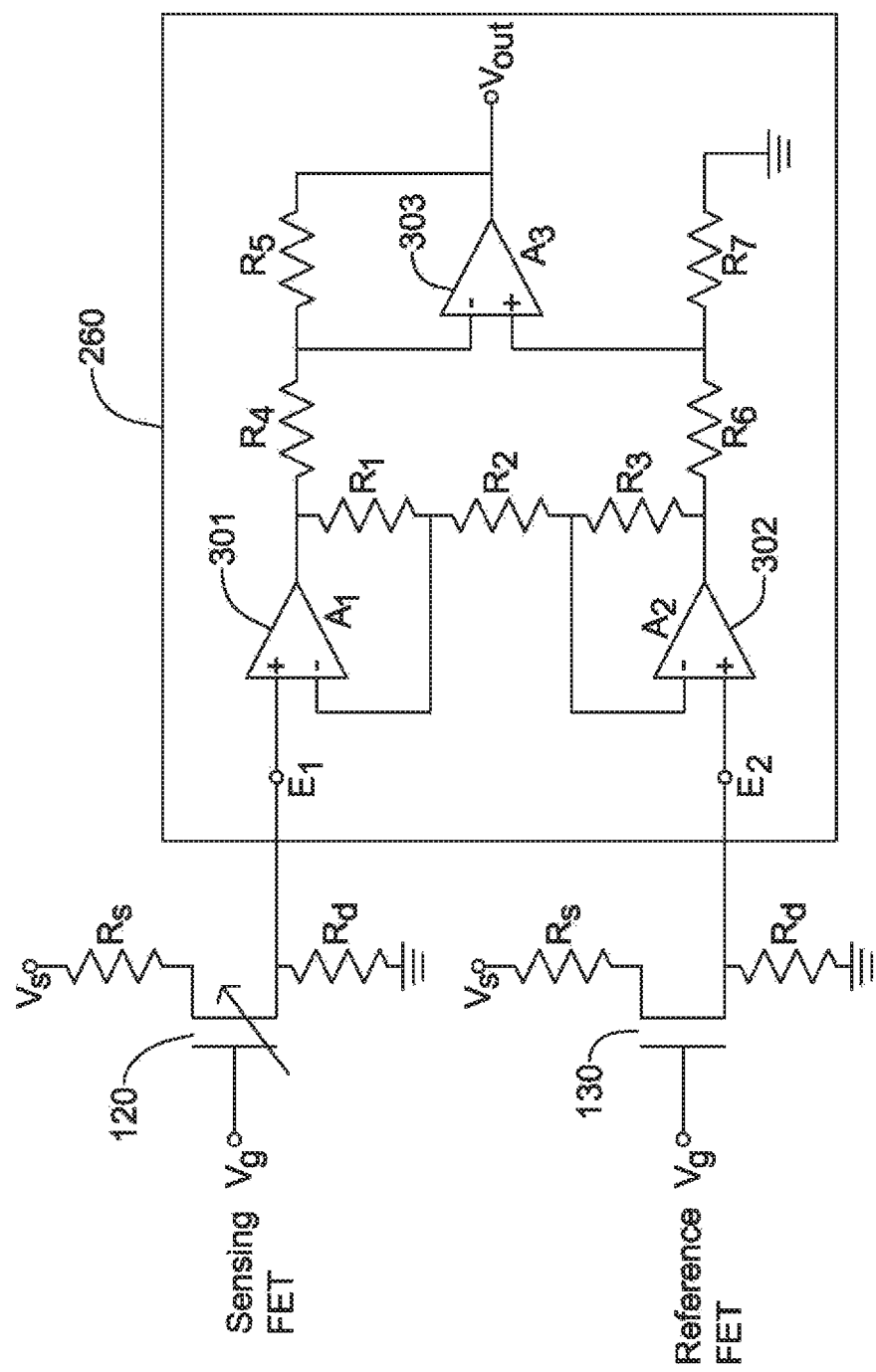
FIG. 2 is a schematic diagram of an illustrative sensing circuit for use with the illustrative humidity sensor of FIG. 1.

FIG. 2 is a schematic diagram of an illustrative sensing circuit for use with the illustrative humidity sensor of FIG. 1. The circuitry may differentially amplify signals of the sensing FET 120 and the reference FET 130 to form a differential humidity sensor. Reference numeral 260 may indicate a circuit or an instrumentation amplifier incorporating three operational amplifiers 301, 302 and 303 connected to produce a high common mode rejection ratio (CMRR) of greater than 50 dB. Circuit 260 may be designed to interface with p-channel FETs and/or n-channel FETs.

In FIG. 2, $E_1$ and $E_2$ denote output voltages of the sensing FET 120 and the reference FET 130, respectively. In some cases, the gate electrodes of the sensing FET 120 and the reference FET 130 may be driven using a common gate voltage Vg that operates the sensing FET 120 and the reference FET 130 in their linear region. The resistors $R_1$-$R_7$ may be selected to satisfy the conditions of $R_5/R_4=R_7/R_6=k$ and $2*(R_1/R_2)=2*(R_3/R_2)=G$ such that $R_1=R_3$, resulting in an output voltage $V_{out}=-k*(G+1)*(E_1-E_2)=$Differential Gain$*(E_1-E_2)$, while the common mode rejection ratio (CMRR) approaches infinity and the common mode gain may be theoretically zero and actually virtually zero. In this example, the differential gain may be changed by changing $R_2$ without affecting the CMRR. This differential approach ($V_{out}=$Differential Gain$*(E_1-E_2)$) may minimize sensor drift by subtracting the common mode signals produced from factors such as temperature, polymer ageing, electronic noise, as well as other factors.

During use, the value of voltage $E_1$ may be different from $E_2$, due to water vapor absorption in the humidity sensing layer 140 of the sensing FET 120. Such water vapor may increase the dielectric constant of the humidity sensing layer 140 and also changes the work function difference of the FET, which change the threshold voltage of the sensing FET 120. This affects the drain current of the sensing FET 120 for a given source, drain and gate voltage. As described above with respect to FIG. 1, the water vapor will not enter the reference FET, so the $E_2$ voltage value will only be effected by common mode factors (e.g., temperature, ageing, noise)

but not humidity changes. In some cases, differential amplification of the signals produced by the sensing FET 120 and reference FET 130 may be implemented on the same chip as the sensing and reference FETs 120, 130, but this is not required.

In some cases, sensing and reference n-channel FETs 120, 130 may be fabricated using conventional integrated circuit processes. In one example, a relatively thick (1.5 to 2 microns) thermal silicon oxide layer 160 may be formed on a p-type silicon substrate 110 followed by selective etching of the thermal silicon oxide layer 160 to form windows at the source, drain and gate regions of the sensing and reference n-channel FETs 120, 130. Phosphorus atoms may then be implanted/diffused into the substrate to create n-doped regions forming the sources and drains of the reference and sensing FETs 120, 130.

A lower gate dielectric layer 126 of silicon dioxide, or other appropriate gate insulator material, may be thermally grown over the substrate followed by masking and etching to define gate regions. Growth of a thin silicon dioxide gate insulator layer, or other appropriate gate insulator material, may form the lower gate dielectric layer and help assure a good surface state density at the silicon dioxide/silicon substrate interface. A barrier layer 128, 138, such as $Ta_2O_5$, $Al_2O_3$, $HfO_2$, or $Si_3N_4$, may be disposed over the lower gate insulating layer 126, 136. The barrier layer 128, 138 and the lower gate insulating layer 126, 136 may be removed from the source and drain contact regions. A platinum layer may be sputter coated and pattered to form the source and drain contact electrodes 142, 144, 152, 154.

A humidity sensing layer 140, 150 may be applied above the barrier layer 128, 138. In some cases, one of the suitable hydrophobic polymers identified herein may be applied over the barrier layer 128, 138, for example, by spin coating and drying/heating. The polymer layer may be soft baked in air at 90-150° C. and then photoresist patterned to define the hydrophobic polymer layer of the gate stack before curing at up to 400 degrees C. in a dry nitrogen atmosphere.

A porous metal (e.g., gold, platinum) layer may be applied (e.g. sputtered) over the hydrophobic polymer layer of the gate stack of the sensing FET 120. A thick dense metal (gold, platinum) layer may be applied over the hydrophobic polymer layer of the gate of the reference FET 130. In some instances, a thin layer of chromium may be deposited prior to the application of the gate metal layer(s) to improve adhesion. Sputtering and patterning of an aluminum (or other conductive material) layer for contacting the source, drain, and gate electrodes may complete the fabrication of the sensing and reference FETs 120, 130.

One of the suitable hydrophobic polymers identified herein may then be applied as the protective porous hydrophobic dielectric polymer layer 162 by, for example, spin coating and drying/heating. The polymer layer may be soft baked in air at 90-150° C. A passivation layer 164 of barrier material may then be deposited over the protective porous hydrophobic dielectric polymer layer 162 and patterned such that the passivation layer 164 does not cover the sensing FET 120 gate stack. The protective porous hydrophobic dielectric polymer layer 162 and the passivation layer 164 may be selectively removed to provide a pathway to the gate electrodes 146, 156. A Ti/Au layer may be sputtered and patterned to define gate contacts 148, 158 for contacting the gate regions.

One or more of these steps may be modified if it is desirable to employ FETs implemented using different technologies, for example, n-MOS, p-MOS, CMOS, and so on. Similarly, one or more additional process steps may be employed if it is desirable to fabricate an instrumentation amplifier on the same substrate.

The disclosure should not be considered limited to the particular examples described above. Various modifications, equivalent processes, as well as numerous structures to which the disclosure can be applicable will be readily apparent to those of skill in the art upon review of the instant specification.

What is claimed is:

1. A humidity sensor comprising:
   a substrate having a source and a drain, wherein the drain is laterally spaced from the source;
   a gate stack comprising:
      a gate insulator situated in the space between the source and the drain;
      a barrier positioned over the gate insulator;
      a sensing polymer positioned over the barrier;
   a source electrode electrically coupled to the source;
   a drain electrode electrically coupled to the drain;
   a porous gate electrode positioned over the sensing polymer; and
   a protective porous polymer layer that extends over the porous gate electrode.

2. The humidity sensor of claim 1, wherein:
   the substrate comprises silicon;
   the gate insulator comprises $SiO_2$.

3. The humidity sensor of claim 2, wherein the barrier comprises one or more of $Ta_2O_5$, $Al_2O_3$, $HfO_2$ and silicon nitride ($Si_3N_4$).

4. The humidity sensor of claim 1, wherein the sensing polymer comprises a polyimide.

5. The humidity sensor of claim 1, wherein the sensing polymer comprises a polysulfone.

6. The humidity sensor of claim 1, wherein the sensing polymer comprises at least one of a polyimide and a polysulfone which has been cross-linked using one member of:
   2,2,3,3,4,4,5,5-octafluoro-1,6-hexanediol;
   1,5-pentanediol;
   1,10-decanediol; and
   1,4-benzenedimethanol.

7. The humidity sensor of claim 1, wherein the sensing polymer comprises a reaction product of a polysulfone with bis(pinacolato)diboron and diterbutylbipyridine in a presence of an iridium catalyst followed by reaction with 4-formyl-4'-bromo diphenyl in a presence of a palladium catalyst followed by mild oxidation and crosslinking with octofluorohexanediol.

8. The humidity sensor of claim 1, wherein the barrier comprises a metal oxide.

9. The humidity sensor of claim 8, wherein the metal oxide comprises $Ta_2O_5$, $Al_2O_3$, or $HfO_2$.

10. The humidity sensor of claim 1, wherein the barrier comprises silicon nitride ($Si_3N_4$).

11. The humidity sensor of claim 1, further comprising a passivation layer over a portion of the protective porous polymer layer.

12. The humidity sensor of claim 11, wherein the passivation layer does not extend over at least part of the protective porous polymer layer that is over the porous gate electrode.

13. The humidity sensor of claim 11, wherein the passivation layer comprises $SiO_2$, $Ta_2O_5$, $Al_2O_3$, $HfO_2$, or silicon nitride ($Si_3N_4$).

14. A humidity sensor comprising:
   a silicon substrate having a source and a drain, wherein the drain is laterally spaced from the source;

a gate stack comprising:
- an $SiO_2$ gate insulator situated in the space between the source and the drain;
- a barrier positioned over the $SiO_2$ gate insulator, the barrier comprising one or more of $Ta_2O_5$, $Al_2O_3$, $HfO_2$ and silicon nitride ($Si_3N_4$);
- a sensing polymer positioned over the barrier, the sensing polymer comprising at least one of a polyimide and a polysulfone which has been cross-linked using one member of:
  - 2,2,3,3,4,4,5,5-octafluoro-1,6-hexanediol;
  - 1,5-pentanediol;
  - 1,10-decanediol;
  - 1,4-benzenedimethanol;

a source electrode electrically coupled to the source;
a drain electrode electrically coupled to the drain;
a porous gate electrode positioned over the sensing polymer; and
a protective porous polymer layer that extends over the porous gate electrode.

15. The humidity sensor of claim 14, further comprising a passivation layer over a portion of the protective porous polymer layer.

16. The humidity sensor of claim 15, wherein the passivation layer does not extend over at least part of the protective porous polymer layer that is over the porous gate electrode.

17. The humidity sensor of claim 15, wherein the passivation layer comprises $SiO_2$, $Ta_2O_5$, $Al_2O_3$, $HfO_2$, or silicon nitride ($Si_3N_4$).

18. The humidity sensor of claim 14, further comprising:
a reference field effect transistor formed on the substrate.

19. The humidity sensor of claim 18, wherein the reference field effect transistor comprises:
- a second source and a second drain formed on the substrate, wherein the second drain is laterally spaced from the second source;
- a second gate stack comprising:
  - a second gate insulator situated in the space between the second source and the second drain;
  - a second barrier positioned over the second gate insulator;
  - a second sensing polymer positioned over the second barrier;
- a second source electrode electrically coupled to the second source;
- a second drain electrode electrically coupled to the second drain; and
- a metal layer positioned over the second sensing polymer.

20. The humidity sensor of claim 14, wherein the metal layer is configured to prevent the second sensing polymer from being exposed to the environment.

* * * * *